US009165357B2

(12) United States Patent
Dylewski

(10) Patent No.: US 9,165,357 B2
(45) Date of Patent: Oct. 20, 2015

(54) METHODS FOR DETERMINING A WAVEFRONT POSITION ON A TEST STRIP

(71) Applicant: Alverix, Inc., San Jose, CA (US)

(72) Inventor: Scott Dylewski, Sunnyvale, CA (US)

(73) Assignee: Alverix, Inc., San Jose, CA (US)

( * ) Notice: Subject to any disclaimer, the term of this patent is extended or adjusted under 35 U.S.C. 154(b) by 201 days.

(21) Appl. No.: 13/804,248

(22) Filed: Mar. 14, 2013

(65) Prior Publication Data

US 2013/0195332 A1     Aug. 1, 2013

Related U.S. Application Data

(62) Division of application No. 12/354,141, filed on Jan. 15, 2009, now Pat. No. 8,422,740.

(51) Int. Cl.
| | | |
|---|---|---|
| *G01F 1/708* | (2006.01) | |
| *G06T 7/00* | (2006.01) | |
| *G01N 21/84* | (2006.01) | |
| *G01N 21/78* | (2006.01) | |

(52) U.S. Cl.
CPC ............ *G06T 7/0012* (2013.01); *G01F 1/7086* (2013.01); *G01N 21/78* (2013.01); *G01N 21/8483* (2013.01)

(58) Field of Classification Search
CPC ........... B01L 2300/0825; G01N 21/78; G01N 21/8483; G01N 2015/1075; G01N 2021/8488; G06T 7/20; G06T 7/2053; G06T 7/2086
See application file for complete search history.

(56) References Cited

U.S. PATENT DOCUMENTS

| | | |
|---|---|---|
| 3,905,767 A | 9/1975 | Morris et al. |
| 3,915,647 A | 10/1975 | Wright |
| 4,197,088 A | 4/1980 | Meserol et al. |
| 4,267,261 A | 5/1981 | Hallman et al. |
| 4,275,149 A | 6/1981 | Litman et al. |
| 4,299,916 A | 11/1981 | Litman et al. |
| 4,366,241 A | 12/1982 | Tom et al. |
| 4,400,353 A | 8/1983 | Meserol et al. |
| 4,491,012 A | 1/1985 | Peterson |
| 4,647,544 A | 3/1987 | Nicoli et al. |
| 4,666,309 A | 5/1987 | Barry et al. |
| 4,757,004 A | 7/1988 | Houts et al. |
| 4,806,311 A | 2/1989 | Greenquist |
| 4,818,677 A | 4/1989 | Hay-Kaufman et al. |
| 4,943,522 A | 7/1990 | Eisinger et al. |
| 5,039,607 A | 8/1991 | Skold et al. |
| 5,075,078 A | 12/1991 | Osikowicz et al. |

(Continued)

FOREIGN PATENT DOCUMENTS

| | | |
|---|---|---|
| EP | 0291194 | 11/1988 |
| EP | 0653625 | 5/1995 |

*Primary Examiner* — David A Rogers
(74) *Attorney, Agent, or Firm* — Knobbe, Martens, Olson & Bear LLP

(57) ABSTRACT

The present disclosure relates to methods for determining a wavefront position of a liquid on a surface of an assay test strip placing a liquid on the surface of the test strip; and acquiring one or more signals from the surface of the test strip at one or more times, comparing the one or more acquired signals to a threshold, wherein the wavefront position is a position on the surface of the test strip where a signal is greater than or less than a threshold (e.g., fixed or dynamic threshold). Such methods may be used to determine the wavefront velocity of a liquid on a surface of an assay test strip and the transit time of a liquid sample to traverse the one or more positions on the surface of the assay test strip.

11 Claims, 1 Drawing Sheet

(56) References Cited

U.S. PATENT DOCUMENTS

| | | | |
|---|---|---|---|
| 5,094,955 | A | 3/1992 | Calandra et al. |
| 5,096,837 | A | 3/1992 | Fan et al. |
| 5,118,183 | A | 6/1992 | Cargill et al. |
| 5,118,428 | A | 6/1992 | Sand et al. |
| 5,118,630 | A | 6/1992 | Glaze |
| 5,132,097 | A | 7/1992 | Van Deusen et al. |
| 5,198,369 | A | 3/1993 | Itoh et al. |
| 5,221,616 | A | 6/1993 | Kolb et al. |
| 5,223,220 | A | 6/1993 | Fan et al. |
| 5,225,328 | A | 7/1993 | Chang |
| 5,252,459 | A | 10/1993 | Tarcha et al. |
| 5,415,994 | A | 5/1995 | Imrich et al. |
| 5,434,057 | A | 7/1995 | Dorian |
| 5,457,313 | A | 10/1995 | Baylor et al. |
| 5,500,375 | A | 3/1996 | Lee-Own et al. |
| 5,521,102 | A | 5/1996 | Boehringer et al. |
| RE35,306 | E | 7/1996 | Chen et al. |
| 5,536,646 | A | 7/1996 | Sand et al. |
| 5,541,069 | A | 7/1996 | Mortensen et al. |
| 5,586,202 | A | 12/1996 | Ohki et al. |
| 5,591,645 | A | 1/1997 | Rosenstein |
| 5,598,007 | A | 1/1997 | Bunce et al. |
| 5,656,502 | A | 8/1997 | MacKay et al. |
| 5,658,801 | A | 8/1997 | Poissant et al. |
| 5,661,563 | A | 8/1997 | Howard et al. |
| 5,686,315 | A | 11/1997 | Pronovost et al. |
| 5,706,416 | A | 1/1998 | Mann et al. |
| 5,763,262 | A | 6/1998 | Wong et al. |
| 5,766,961 | A | 6/1998 | Pawlak et al. |
| 5,770,460 | A | 6/1998 | Pawlak et al. |
| 5,773,234 | A | 6/1998 | Pronovost et al. |
| 5,786,220 | A | 7/1998 | Pronovost et al. |
| 5,787,901 | A | 8/1998 | Wilson |
| 5,804,452 | A | 9/1998 | Pronovost et al. |
| 5,814,455 | A | 9/1998 | Pronovost et al. |
| 5,930,406 | A | 7/1999 | Itsuzaki et al. |
| 5,939,331 | A | 8/1999 | Burd et al. |
| 5,991,697 | A | 11/1999 | Nelson et al. |
| 6,049,619 | A | 4/2000 | Anandan et al. |
| 6,277,281 | B1 | 8/2001 | Ditter et al. |
| 6,306,642 | B1 | 10/2001 | Nelson et al. |
| 6,352,862 | B1 | 3/2002 | Davis et al. |
| 6,602,719 | B1 | 8/2003 | Carpenter |
| 6,967,105 | B2 | 11/2005 | Nomura et al. |
| 7,262,857 | B2 | 8/2007 | Koike |
| 7,264,627 | B2 | 9/2007 | Perez |
| 7,547,557 | B2 | 6/2009 | LaBorde et al. |
| 7,593,560 | B2 | 9/2009 | Hasson et al. |
| 7,622,715 | B2 | 11/2009 | Ignatowicz |
| 7,888,130 | B2 | 2/2011 | Wuske et al. |
| 7,920,959 | B1 | 4/2011 | Williams |
| 8,422,740 | B2 | 4/2013 | Dylewski |
| 2003/0060730 | A1 | 3/2003 | Perez |
| 2005/0189224 | A1 | 9/2005 | Parce |
| 2006/0169032 | A1 | 8/2006 | Sutton |
| 2006/0204399 | A1 | 9/2006 | Freeman et al. |
| 2007/0000629 | A1 | 1/2007 | Tirimacco et al. |
| 2007/0016153 | A1 | 1/2007 | Hird et al. |
| 2008/0130971 | A1 | 6/2008 | Hasson et al. |
| 2008/0176068 | A1 | 7/2008 | Neubert et al. |
| 2009/0246886 | A1 | 10/2009 | Buck |
| 2010/0172802 | A1 | 7/2010 | Sharrock et al. |
| 2012/0083044 | A1* | 4/2012 | Sturman et al. ............ 436/165 |

* cited by examiner

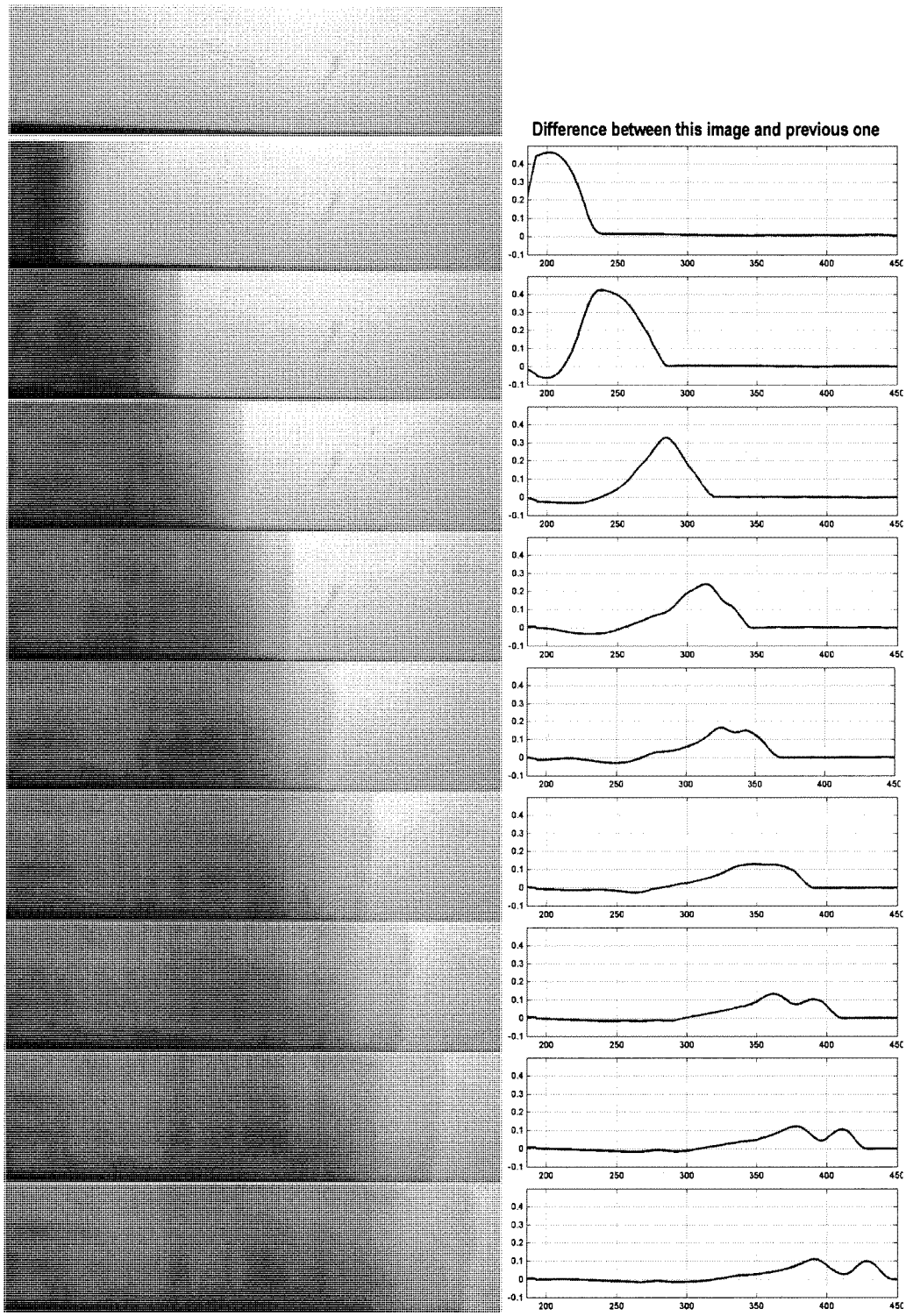

METHODS FOR DETERMINING A WAVEFRONT POSITION ON A TEST STRIP

BACKGROUND

Assay test kits currently are available for testing a wide variety of medical and environmental conditions or compounds, such as a hormone, a metabolite, a toxin, or a pathogen-derived antigen. Most commonly these tests are used for medical diagnostics either for home testing, point of care testing, or laboratory use. For example, lateral flow tests are a form of immunoassay in which the test sample flows along a solid substrate via capillary action. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

A common problem with lateral flow test strips is that different test strips tend to produce slightly different results. Unfortunately, no two test strips will perform exactly alike (i.e. generate identical test result values) even if the test strips have the same amount of reagent embedded therein, and even if they are both exposed to the same amount of analyte. Such discrepancies in lateral flow assay test results may be due to differences in the physical properties of individual test strips, and also by differences in the fluid flow path along different test strips.

SUMMARY

The present disclosure relates generally to methods for determining a wavefront position of a liquid (e.g., a liquid test sample) on a surface of a test strip (e.g., lateral flow test strip). Such methods may be used to determine the transit time of a liquid across the surface of an assay test strip or the start time of an assay.

The present disclosure relates generally to methods for determining a wavefront position of a liquid on a surface of a test strip by placing a liquid on the surface of the test strip; acquiring one or more signals from the surface of the test strip at one or more times; and comparing the one or more acquired signals to a threshold, wherein the wavefront position is a position on the surface of the test strip where a signal is greater than or less than a threshold (e.g., fixed or dynamic threshold).

The present disclosure relates generally to methods for determining a wavefront position of a liquid on a surface of a test strip by placing a liquid on the surface of the test strip; acquiring one or more signals from the surface of the test strip at one or more times; comparing the one or more acquired signals to a threshold, and identifying a signal furthest from where the liquid was placed on the surface of the test strip where a signal is greater than or less than a threshold (e.g., fixed or dynamic threshold).

In an embodiment, the wavefront position is any position on the surface of the test strip where a signal is greater than or less than a threshold. In an embodiment, the wavefront position is a position on the surface of the test strip furthest from where the liquid was placed on the test strip where a signal is greater than or less than a threshold. In an embodiment, the wavefront position is a position on the surface of the test strip where a signal is greater than or less than a threshold and is greater or less than all other signals acquired from the surface of the test strip.

In an embodiment, the one or more acquired signals are subtracted from a constant prior to being compared to the threshold. In an embodiment, the one or more acquired signals are divided by a constant prior to being compared to the threshold. In an embodiment, two acquired signals are compared with each other prior to one signal being compared to the threshold. In an embodiment, two acquired signals are subtracted from each other prior to one signal being compared to the threshold. In an embodiment, a first acquired signal is divided by a second acquired signal prior to the first signal being compared to the threshold.

In an embodiment, the signal is an image. In an embodiment, the image is a picture. In an embodiment, the image is acquired by an image-based detector.

In an embodiment, the test strip is a lateral flow assay test strip.

In an embodiment, the liquid is a test sample.

In an embodiment, the liquid is placed on the surface of the test strip prior to acquisition of a first signal. In an embodiment, the liquid is placed on the surface of the test strip subsequent to acquisition of a first signal.

In an embodiment, a signal acquired prior to the liquid being placed on the surface of the test strip is compared to a signal acquired after the liquid has been placed on the surface of the test strip. In an embodiment, a signal acquired after the liquid being placed on the surface of the test strip is compared to a signal acquired after the liquid has been placed on the surface of the test strip.

In an embodiment, two sequential signals acquired from the surface of the test strip are compared. In an embodiment, two nonsequential signals acquired from the surface of the test strip are compared.

The present disclosure provides methods for determining a wavefront velocity of a liquid on a surface of a test strip by placing a liquid on the surface of the test strip; acquiring signals from the surface of the test strip at two or more times; comparing the one or more acquired signals to a threshold, identifying two signals that are greater than or less than a threshold (e.g., fixed or dynamic threshold); determining the distance between the two acquired signals; and calculating the wavefront velocity by dividing the distance between the two acquired signals by the time between acquisition of the two signals.

The present disclosure provides methods for determining a wavefront velocity of a liquid on a surface of a test strip by placing a liquid on the surface of the test strip; acquiring a first signal from the surface of the test strip at a first time; acquiring a second signal from the surface of the test strip at a second time; comparing the first signal and the second signal; and determining a position furthest from where the liquid was placed on the surface of the test strip where a difference exists between the first and second signal to be the wavefront of the liquid; calculating the amount of time that elapsed between acquisition of the first signal and the second signal; determining the distance traveled by the wavefront from acquisition of the first signal and the second signal; and calculating the wavefront velocity by dividing the distance traveled by the wavefront by the time between acquisition of the first and the second signal.

In an embodiment, the acquired signals are subtracted from a constant prior to being compared to the threshold. In an embodiment, the acquired signals are divided by a constant prior to being compared to the threshold. In an embodiment, two acquired signals are compared with each other prior to one signal being compared to the threshold. In an embodiment, two acquired signals are subtracted from each other prior to one signal being compared to the threshold. In an embodiment, a first acquired signal is divided by a second acquired signal prior to the first signal being compared to the threshold.

In an embodiment, the signal is an image. In a further embodiment, the image is a picture. In an embodiment, the image is acquired by an image-based detector.

In an embodiment, the test strip is a lateral flow assay test strip.

In an embodiment, the liquid is a test sample.

In an embodiment, the liquid is placed on the surface of the test strip prior to acquisition of the first signal. In an other embodiment, the liquid is placed on the surface of the test strip subsequent to acquisition of the first signal.

In an embodiment, a signal acquired prior to the liquid being placed on the surface of the test strip is compared to a signal acquired after the liquid has been placed on the surface of the test strip. In an embodiment, a signal acquired after the liquid being placed on the surface of the test strip is compared to a signal acquired after the liquid has been placed on the surface of the test strip.

In an embodiment, two sequential signals acquired from the surface of the test strip are compared. In an embodiment, two nonsequential signals acquired from the surface of the test strip are compared.

The present disclosure also provides methods for determining a transit time of a liquid to cross the surface of a test strip by acquiring two or more signals from the surface of the test strip; and determining a first signal that is greater than or less than a threshold and a last signal that greater than or less than a threshold, wherein the transit time of the liquid to cross the surface of the test strip is the time between the acquisition of the first signal and the last signal.

In an embodiment, the first signal is acquired from the surface of the test strip. In an embodiment, the first signal is the insertion of the assay test strip into a reader or any mechanical interaction of the test strip with a reader.

The present disclosure also provides methods for determining a transit time of a liquid to advance from a first position on a surface of a test strip to a second position on a surface of a test strip by calculating the wavefront velocity of the liquid as described by the methods of the present disclosure; and determining the transit time of the liquid to cross the surface of the test strip by multiplying the wavefront velocity by the distance separating the first position and second position on the surface of the test strip.

The present disclosure also provides methods for determining a transit time of a liquid to advance from a first position on a test strip to a second position on a surface of an test strip by determining the wavefront velocity of the liquid, comprising acquiring two or more signals from the surface of the test strip at two or more times; identifying at least two signals that are greater than or less than a threshold (e.g., fixed or dynamic threshold); determining the distance between the two or more signals; and calculating the wavefront velocity by dividing the distance between the two or more signals by the time between acquisition of the two or more signals; and calculating the transit time of the liquid to advance from the first position to the second position on the test strip by multiplying the wavefront velocity by the distance separating the first position and second position on the test strip.

The present disclosure also methods for determining a transit time of a liquid to advance from a first position on a test strip to a second position on a surface of an test strip by determining the wavefront velocity of the liquid, comprising placing a liquid on the surface of the test strip; acquiring a first signal from the surface of the test strip at a first time; acquiring a second signal from the surface of the test strip at a second time; comparing the first signal and the second signal; and determining a position furthest from where the liquid was placed on the surface of the test strip where a difference exists between the first and second signal to be the wavefront of the liquid; calculating the amount of time that elapsed between acquisition of the first signal and the second signal; determining the distance traveled by the wavefront from acquisition of the first signal and the second signal; and calculating the wavefront velocity by dividing the distance traveled by the wavefront by the time between acquisition of the first and the second signal; and calculating the transit time of the liquid to advance from the first position to the second position on the test strip by multiplying the wavefront velocity by the distance separating the first position and second position on the test strip.

The present disclosure also provides methods for determining a starting time for a test assay by placing a liquid on the surface of the test strip; acquiring one or more signals from the surface of the test strip at one or more times; comparing the one or more acquired signals to a threshold, wherein the starting time is determined as the time at which a first signal is acquired that is greater than or less than a threshold.

In an embodiment, the one or more acquired signals are subtracted from a constant prior to being compared to the threshold. In an embodiment, the one or more acquired signals are divided by a constant prior to being compared to the threshold. In an embodiment, two acquired signals are compared with each other prior to one signal being compared to the threshold. In an embodiment, two acquired signals are subtracted from each other prior to one signal being compared to the threshold. In an embodiment, a first acquired signal is divided by a second acquired signal prior to the first signal being compared to the threshold.

In an embodiment, the signal is an image. In a further embodiment, the image is a picture. In an embodiment, the image is acquired by an image-based detector.

In an embodiment, the test strip is a lateral flow assay test strip.

In an embodiment, the liquid is a test sample.

In an embodiment, the methods further comprise acquiring a third image from the surface of the test strip at a third time.

In an embodiment, the liquid is placed on the surface of the test strip prior to acquisition of the first signal. In another embodiment, the liquid is placed on the surface of the test strip subsequent to acquisition of the first signal.

In an embodiment, a signal acquired prior to the liquid being placed on the surface of the test strip is compared to a signal acquired after the liquid has been placed on the surface of the test strip. In an embodiment, a signal acquired after the liquid being placed on the surface of the test strip is compared to a signal acquired after the liquid has been placed on the surface of the test strip.

In an embodiment, two sequential signals acquired from the surface of the test strip are compared. In an embodiment, two nonsequential signals acquired from the surface of the test strip are compared.

In an embodiment, the first position is a sample receiving zone. In an embodiment, the second position is a test zone. In an embodiment, the second position is a control zone. In an embodiment, the first position is a sample receiving zone and the second position is a test zone. In an embodiment, the first position is a sample receiving zone and the second position is a control zone.

Additional features and advantages are described herein, and will be apparent from, the following Detailed Description and figures.

BRIEF DESCRIPTION OF THE FIGURES

FIG. 1 shows images depicting the transit of a wavefront from a liquid sample across the surface of a lateral flow assay test strip. The liquid traversed the test strip from left to right. An exemplary method to determine the wavefront position may be to find the point(s) where the difference plot (right) is larger than a given threshold (e.g., 0.05) and then find the right-most point where the signal is above this level.

DETAILED DESCRIPTION

The present disclosure provides methods and devices for determining the wavefront position of a liquid (e.g. a liquid test sample) on the surface of a lateral flow assay. Variations in flow rate due to variability in the assay membrane or differences in sample viscosity may affect the length of time that an analyte is in contact with bound antibody on the assay surface (e.g., the capture line) and thus may affect the amount of analyte detected by the assay. As such, it is advantageous to determine the wavefront position of a liquid sample to obtain accurate measurements from the lateral flow assay. Such methods of the present disclosure may comprise placing a liquid on the surface of the test strip; and acquiring one or more signals from the surface of the test strip at one or more times, comparing the one or more acquired signals to a threshold, wherein the wavefront position is a position on the surface of the test strip where a signal is greater than or less than a threshold (e.g., fixed or dynamic threshold). The wavefront position may be employed to determine the transit time of the liquid sample to traverse from a first position on the surface of the lateral flow assay to a second position on the surface of the lateral flow assay including, for example, the length of time required for the liquid sample to traverse a first position where the sample comprising an analyte is applied to the assay surface (e.g., a sample pad) to a second position where the analyte is captured by an antibody bound to the surface of the assay surface (e.g., test line). Additionally, the methods of the present disclosure may be used to determine the transit time of a liquid sample to traverse the entire surface of the assay test strip.

The present disclosure provides methods for measuring the flow rate of a liquid (e.g., a liquid test sample) on the surface of an assay test strip. The sample flow rate may be determined by acquiring at least two images from the surface of the lateral flow assay, and calculating the distance that the wavefront has traversed between the acquisition of at least a first and a second image. In the case of left to right flow, the wavefront position is the right most position where the greatest difference exists between two acquired images. The flow rate may then be calculated by dividing the distance that the wavefront has traveled by the time elapsed between the acquisition of the first and the second signal.

In an exemplary method, an image (e.g., a frame) may be acquired from the surface of the assay with an imaging-based detector at regular time intervals (e.g., every second). Each frame $F(n)$ may be compared with frame $F(n-1)$ and the difference in pixels between frames calculated. This difference is the spatial derivative, representing how much each pixel has changed. Positions on the assay surface with the largest change are the positions that have become wet since the acquisition of the previous frame, and positions with little or no change are those positions that have stayed dry or stayed wet. This difference can be calculated by subtracting the two consecutive frames $F(n)-F(n-1)$, or by dividing the two frames $F(n)/F(n-1)$. Images compared do not need to be consecutive. Any two frames that have different acquisition times may be compared. In addition, frames could be compared by also recording their respective acquisition times, and then calculating the derivative as follows: $dF/dt = [F(n)-F(n-1)]/[T(n)-T(n-1)]$, where $F(n)$ is the nth frame, and $T(n)$ is the time that the nth frame was acquired. These calculations can be made using the full 2-D image, or a 1-D representation of the image after it has been summed or average over each column.

The methods of the present disclosure may be used to determine the transit time for a liquid sample to traverse a distance between two positions on the surface of the assay including, for example, the entire surface of the assay.

The methods of the present disclosure are preferably used with an immunoassay device. One or more analytes bound to an antibody on the surface of the immunoassay device may be detected and subsequently quantitated.

Exemplary assays contemplated for use with the methods of the present disclosure include lateral flow assay test strips. Lateral flow assay test strips may comprise a membrane system that forms a single fluid flow pathway along the test strip. The membrane system may include one or more components that act as a solid support for immunoreactions. For example, porous, bibulous or absorbent materials may be placed on a strip such that they partially overlap, or a single material can be used, in order to conduct liquid along the strip. The membrane materials may be supported on a backing, such as a plastic backing. In a preferred embodiment, the test strip includes a glass fiber pad, a nitrocellulose strip and an absorbent cellulose paper strip supported on a plastic backing.

Antibodies that react with the target analyte and/or a detectable label system are immobilized on the solid support. The antibodies may be bound to the test strip by adsorption, ionic binding, van der Waals adsorption, electrostatic binding, or by covalent binding, by using a coupling agent, such as glutaraldehyde. For example, the antibodies may be applied to the conjugate pad and nitrocellulose strip using standard dispensing methods, such as a syringe pump, air brush, ceramic piston pump or drop-on-demand dispenser. In a preferred embodiment, a volumetric ceramic piston pump dispenser may be used to stripe antibodies that bind the analyte of interest, including a labeled antibody conjugate, onto a glass fiber conjugate pad and a nitrocellulose strip. The test strip may or may not be otherwise treated, for example, with sugar to facilitate mobility along the test strip or with water-soluble non-immune animal proteins, such as albumins, including bovine serum albumin (BSA), other animal proteins, water-soluble polyamino acids, or casein to block non-specific binding sites.

Any antibody, including polyclonal or monoclonal antibodies, or any fragment thereof, such as the Fab fragment, that binds the analyte of interest, is contemplated for use herein.

An antibody conjugate containing a detectable label may be used to bind the analyte of interest. The detectable label used in the antibody conjugate may be any physical or chemical label capable of being detected on a solid support using a reader, preferably a reflectance reader, and capable of being used to distinguish the reagents to be detected from other compounds and materials in the assay.

Suitable antibody labels are well known to those of skill in the art and include, but are not limited to, enzyme-substrate combinations that produce color upon reaction, colored particles, such as latex particles, colloidal metal or metal or carbon sol labels, fluorescent labels, and liposome or polymer sacs, which are detected due to aggregation of the label. In an embodiment, colloidal gold is used in the labeled antibody conjugate. The label may be derivatized for linking antibodies, such as by attaching functional groups, such as carboxyl groups to the surface of a particle to permit covalent attachment of antibodies. Antibodies may be conjugated to the label using well known coupling methods.

The assay test strip may be any conventional lateral flow assay test strip such as disclosed in EP 291194 or U.S. Pat. No. 6,352,862. The test strip may comprise a porous carrier containing a particulate labeled specific binding reagent and an unlabelled specific binding reagent. The light sources and corresponding photodetectors are preferably so aligned such that during use, light from the light source or sources falls upon the respective zones on the porous carrier and is reflected or transmitted to the respective photodetectors. The photodetectors generate a current roughly proportional to the amount of light falling upon it which is then fed through a resistor to generate a voltage. The amount of light reaching the photodetector depends upon the amount of colored particulate label present and therefore the amount of analyte. Thus the amount of analyte present in the sample may be determined. This method of optically determining the analyte concentration is described more fully in EP 653625.

A sample may include, for example, anything which may contain an analyte of interest. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cells.

A fluid sample (e.g., biological fluid) may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

Exemplary lateral flow devices include those described in U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5939,331, 6,306,642.

A sample may include, for example, anything which may contain an analyte. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). A liquid sample may refer to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte.

An analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof (see, e.g., U.S. Pat. Nos. 4,366,241; 4,299,916; 4,275,149; and 4,806,311).

In an embodiment, a sample receiving zone on the surface of a lateral flow assay test strip accepts a fluid sample that may contain one or more analytes of interest. In an embodiment, the sample receiving zone is dipped into a fluid sample. A label zone is located downstream of the sample receiving zone, and contains one or more mobile label reagents that recognize, or are capable of binding the analytes of interest. Further, a test region may be disposed downstream from the label zone, and contains test and control zones. The test zone(s) generally contain means which permit the restraint of a particular analyte of interest in each test zone. Frequently, the means included in the test zone(s) comprise an immobilized capture reagent that binds to the analyte of interest. Generally the immobilized capture reagent specifically binds to the analyte of interest. Thus, as the fluid sample flows along the matrix, the analyte of interest will first bind with a mobilizable label reagent in the label zone, and then become restrained in the test zone.

In an embodiment, the sample receiving zone may be comprised of an absorbent application pad. Suitable materials for manufacturing absorbent application pads include, but are not limited to, hydrophilic polyethylene materials or pads, acrylic fiber, glass fiber, filter paper or pads, desiccated paper, paper pulp, fabric, and the like. For example, the sample receiving zone may be comprised of a material such as a nonwoven spunlaced acrylic fiber.

The sample receiving zone may be comprised of any material from which the fluid sample can pass to the label zone. Further, the absorbent application pad can be constructed to act as a filter for cellular components, hormones, particulate, and other certain substances that may occur in the fluid sample. Application pad materials suitable for use by the present invention also include those application pad materials disclosed in U.S. Pat. No. 5,075,078.

In a further embodiment, the sample receiving zone may be comprised of an additional sample application member (e.g., a wick). Thus, in one aspect, the sample receiving zone can comprise a sample application pad as well as a sample application member. Often the sample application member is comprised of a material that readily absorbs any of a variety of fluid samples contemplated herein, and remains robust in physical form. Frequently, the sample application member is comprised of a material such as white bonded polyester fiber. Moreover, the sample application member, if present, is positioned in fluid-flow contact with a sample application pad.

In an embodiment, the label zone material may be treated with labeled solution that includes material-blocking and label-stabilizing agents. Blocking agents include, for example, bovine serum albumin (BSA), methylated BSA, casein and nonfat dry milk. Stabilizing agents are readily available and well known in the art, and may be used, for example, to stabilize labeled reagents.

The label zone may contain a labeled reagent, often comprising one or more labeled reagents. In many of the presently contemplated embodiments, multiple types of labeled reagents are incorporated in the label zone such that they may permeate together with a fluid sample contacted with the device. These multiple types of labeled reagent can be analyte specific or control reagents and may have different detectable characteristics (e.g., different colors) such that one labeled reagent can be differentiated from another labeled reagent if utilized in the same device. As the labeled reagents are frequently bound to a specific analyte of interest subsequent to fluid sample flow through the label zone, differential detection of labeled reagents having different specificities (including analyte specific and control labeled reagents) may be a desirable attribute. However, frequently, the ability to differentially detect the labeled reagents having different specificities based on the label component alone is not necessary due to the presence of test and control zones in the device, which allow for the accumulation of labeled reagent in designated zones.

The labeling zone may also include control-type reagents. These labeled control reagents often comprise detectable moieties that will not become restrained in the test zones and that are carried through to the test region and control zone(s) by fluid sample flow through the device. In a frequent embodiment, these detectible moieties are coupled to a member of a specific binding pair to form a control conjugate which can then be restrained in a separate control zone of the test region by a corresponding member of the specific binding pair to verify that the flow of liquid is as expected. The visible moieties used in the labeled control reagents may be the same or different color, or of the same or different type, as those used in the analyte of interest specific labeled reagents. If different colors are used, ease of observing the results may be enhanced.

The test region may include a control zone for verification that the sample flow is as expected. Each of the control zones comprise a spatially distinct region that often includes an immobilized member of a specific binding pair which reacts with a labeled control reagent. In an occasional embodiment, the procedural control zone contains an authentic sample of the analyte of interest, or a fragment thereof. In this embodiment, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another embodiment, the control line contains antibody that is specific for, or otherwise provides for the immobilization of, the labeled reagent. In operation, a labeled reagent is restrained in each of the one or more control zones, even when any or all the analytes of interest are absent from the test sample.

Since the devices of the present invention may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest. In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in an amount that allows for the generation of desired signal intensity in the one or more control zones, and allows each of the control zones to restrain a desired amount of labeled control-reagent. At the completion of an assay, each of the control zones preferably provide a desired and/or pre-designed signal (in intensity and form).

In an embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectible signal (e.g., be of the same color) or provide distinguishable detectible signals (e.g., have different colored labels or other detection systems) upon accumulation in the control zone(s).

In an embodiment, the labeled control reagent comprises a detectible moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

The use of a control zone is helpful in that appearance of a signal in the control zone indicates the time at which the test result can be read, even for a negative result. Thus, when the expected signal appears in the control line, the presence or absence of a signal in a test zone can be noted.

Test zones of the present description include means that permit the restraint of an analyte of interest. Frequently, test zones of the present description include a ligand that is capable of specifically binding to an analyte of interest. Alternatively, test zones of the present description include a ligand that is capable of specifically binding the labeled reagent bound to an analyte of interest. In practice, a labeled test reagent binds an analyte of interest present in a fluid sample after contact of the sample with a representative device and flow of the fluid sample into and through the label zone. Thereafter, the fluid sample containing the labeled analyte progresses to a test zone and becomes restrained in the test zone. The accumulation of labeled analyte in the test zone produces a detectible signal. Devices may incorporate one or more test zones, each of which is capable of restraining different analytes, if present, in a fluid sample. Thus, in representative embodiments two, three, four, five or more (labeled) analytes of interest can be restrained in a single or different test zones, and thereby detected, in a single device.

The present devices may optionally further comprise an absorbent zone that acts to absorb excess sample after the sample migrates through the test region. The absorbent zone, when present lies in fluid flow contact with the test region. This fluid flow contact can comprise an overlapping, abutting or interlaced type of contact. In an occasional embodiment, a control region (end of assay indicator) is provided in the absorbent zone to indicate when the assay is complete. In this embodiment, specialized reagents are utilized, such as pH sensitive reagents (such as bromocresol green), to indicate when the fluid sample has permeated past all of the test and control zones.

The test strip optionally may be contained within a housing for insertion into the reflectance reader. The housing may be made of plastic or other inert material that does not interfere with the assay procedure.

The lateral flow assay test strip may be suited for use with a reading device that comprises one or more of the following: a central processing unit (CPU) or microcontroller; two or more LED's; two or more photodiodes; a power source; and associated electrical circuitry. The power source may comprise a battery or any other suitable power source (e.g. a photovoltaic cell). The CPU will typically be programmed so as to determine whether the calculated rate and/or extent of progress of the liquid sample is within predetermined limits.

Conveniently the assay result reading device will comprise some manner of indicating the result of the assay to a user. This may take the form, for example, of an audible or visible signal. Desirably the device will comprise a visual display to display the assay result. This may simply take the form of one or more LED's or other light sources, such that illumination of a particular light source or combination of light sources conveys the necessary information to the user. Alternatively the device may be provided with an alphanumeric or other display, such as an LCD. In addition, or as an alternative, to displaying the assay result, the device may also display or indicate in some other way to the user whether the calculated rate and/or extent of progress of the liquid sample is within the predetermined acceptable limits, and thus whether or not the result of the particular assay should be disregarded. If the reading device determines that a particular assay result should be disregarded it may prompt the user to repeat the assay.

Any device which is compatible for use with an assay test strip, preferably a reflectance reader, for determining the assay result is contemplated for use herein. Such test strip devices as are known to those of skill in the art (see, e.g., U.S. Pat. Nos. 5,658,801, 5,656,502, 5,591,645, 5,500,375, 5,252,459, 5,132,097). Reflectance and other readers, including densitometers and transmittance readers, are known to those of skill in the art (see, e.g., U.S. Pat. Nos. 5,598,007, 5,132,097, 5,094,955, 4,267,261, 5,118,183, 5,661,563, 4,647,544, 4,197,088, 4,666,309, 5,457,313, 3,905,767, 5,198,369, 4,400,353).

While the present disclosure has been described and illustrated herein by references to various specific materials, procedures and examples, it is understood that the disclosure is not restricted to the particular combinations of material and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method for determining a starting time for a test assay, said method comprising;
   placing a liquid on the surface of the test strip;
   acquiring two or more signals from the surface of the test strip at two or more times; and
   comparing the two or more acquired signals to a threshold, wherein the starting time of the assay is determined as the time at which a difference between the two or more acquired signals is greater than or less than a threshold.

2. The method of claim 1, wherein the two or more acquired signals are subtracted from a constant prior to being compared to the threshold.

3. The method of claim 1, wherein the two or more acquired signals are divided by a constant prior to being compared to the threshold.

4. The method of claim 1, wherein two or more acquired signals are compared with each other prior to being compared to the threshold.

5. The method of claim 1, wherein two or more acquired signals are subtracted from each other prior to being compared to the threshold.

6. The method of claim 1, wherein a first acquired signal is divided by a second acquired signal prior to being compared to the threshold.

7. The method of claim 1, wherein the signal is an image.

8. The method of claim 7, wherein the image is a picture.

9. The method of claim 1, wherein the image is acquired by an image-based detector.

10. The method of claim 1, wherein the test strip is a lateral flow assay test strip.

11. The method of claim 1, wherein the liquid is a test sample.

\* \* \* \* \*